United States Patent
McCrea et al.

(10) Patent No.: US 8,137,605 B2
(45) Date of Patent: *Mar. 20, 2012

(54) METHODS FOR MAKING AN ENCAPSULATED STENT

(75) Inventors: Brendan McCrea, Ballwin, MO (US); Tarun J. Edwin, Chandler, AZ (US); Christopher E. Banas, Mesa, AZ (US)

(73) Assignee: Bard Peripheral Vascular, Inc., Tempe, AZ (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/088,129

(22) Filed: Apr. 15, 2011

(65) Prior Publication Data

US 2011/0196473 A1 Aug. 11, 2011

Related U.S. Application Data

(60) Continuation of application No. 12/272,411, filed on Nov. 17, 2008, now Pat. No. 7,939,000, which is a continuation of application No. 10/873,085, filed on Jun. 21, 2004, now Pat. No. 7,468,071, which is a continuation of application No. 10/000,583, filed on Oct. 24, 2001, now Pat. No. 6,758,858, which is a division of application No. 08/833,797, filed on Apr. 9, 1997, now Pat. No. 6,451,047, which is a continuation-in-part of application No. 08/508,033, filed on Jul. 27, 1995, now Pat. No. 5,749,880, which is a continuation-in-part of application No. 08/401,871, filed on Mar. 10, 1995, now Pat. No. 6,124,523, which is a continuation-in-part of application No. 08/794,871, filed on Feb. 5, 1997, now Pat. No. 6,039,755.

(51) Int. Cl.
B29C 45/14 (2006.01)

(52) U.S. Cl. .................. 264/229; 623/1.13; 623/1.27

(58) Field of Classification Search .................. 264/229; 606/191, 108, 198, 194–195; 623/1.13, 1.27, 623/23.7, 23.71, 1.1, 901
See application file for complete search history.

(56) References Cited

U.S. PATENT DOCUMENTS

| | | | | | |
|---|---|---|---|---|---|
| 5,735,892 | A | * | 4/1998 | Myers et al. | 623/1.13 |
| 5,788,626 | A | * | 8/1998 | Thompson | 623/1.15 |
| 5,928,279 | A | * | 7/1999 | Shannon et al. | 623/1.13 |
| 5,961,545 | A | * | 10/1999 | Lentz et al. | 623/1.39 |
| 6,001,125 | A | * | 12/1999 | Golds et al. | 623/23.7 |
| 6,797,217 | B2 | * | 9/2004 | McCrea et al. | 264/229 |
| 7,306,756 | B2 | * | 12/2007 | Edwin et al. | 264/229 |
| 7,468,071 | B2 | * | 12/2008 | Edwin et al. | 623/1.13 |
| 7,939,000 | B2 | * | 5/2011 | Edwin et al. | 264/229 |
| 2004/0232588 | A1 | * | 11/2004 | Edwin et al. | 264/229 |

* cited by examiner

Primary Examiner — Paul Prebilic
(74) Attorney, Agent, or Firm — Rutan & Tucker, LLP

(57) ABSTRACT

A method for making an encapsulated stent includes providing a first seamless unsintered ePTFE tube, providing a second seamless sintered ePTFE tube, positioning a self-expanding stent between the first and second ePTFE tubes to form an assembly, disposing an ePTFE interlayer member between the first and second ePTFE tubes, and joining the first ePTFE tube to the second ePTFE tube through openings in a wall of the stent by applying first pressure, and then heat, to the assembly.

16 Claims, 4 Drawing Sheets

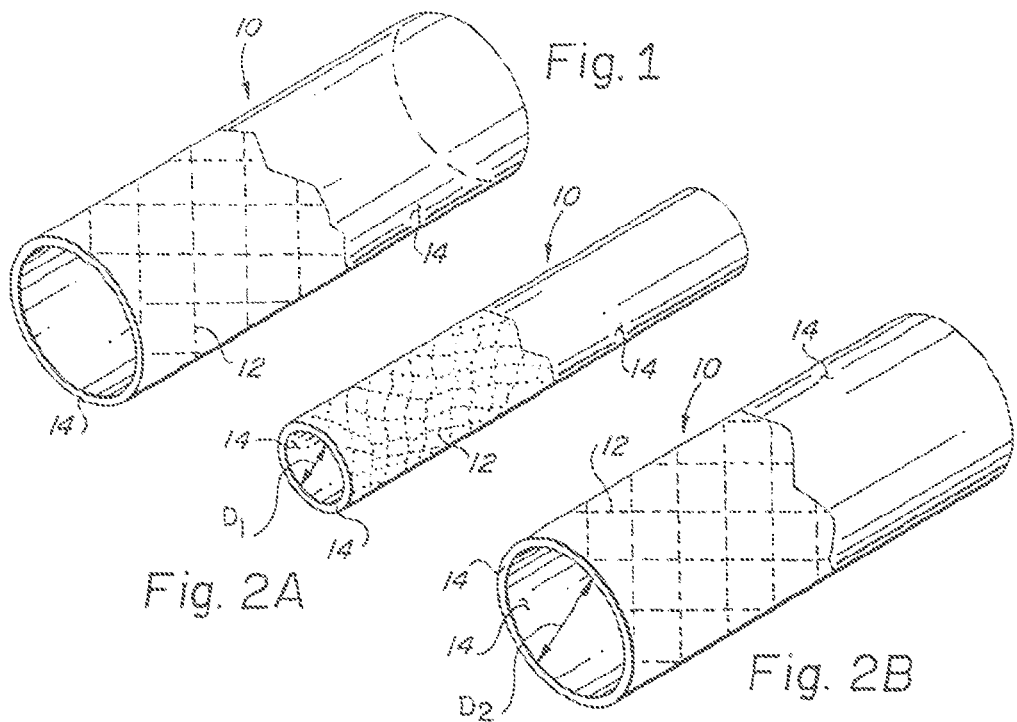
Fig. 1
Fig. 2A
Fig. 2B
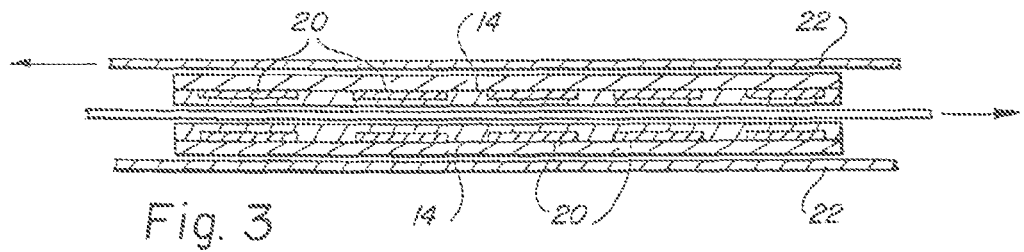
Fig. 3
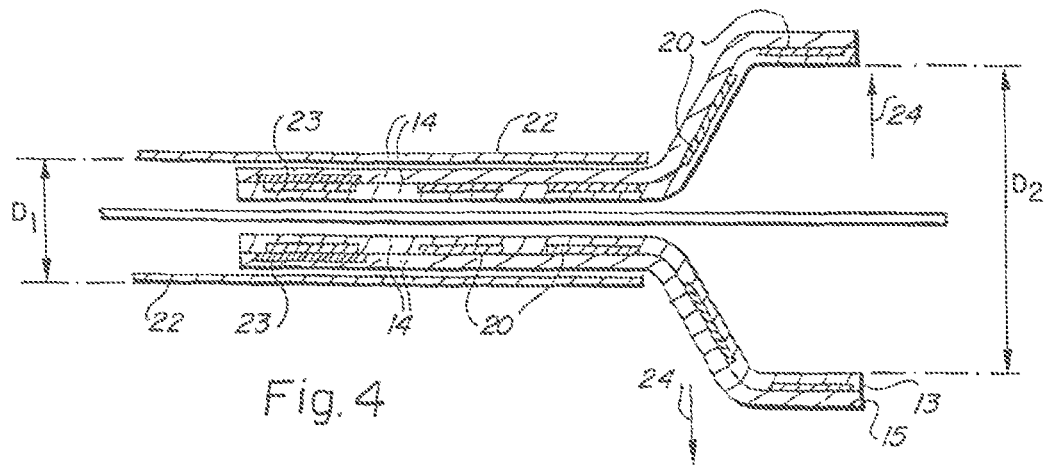
Fig. 4

METHODS FOR MAKING AN ENCAPSULATED STENT

CROSS-REFERENCE TO RELATED APPLICATIONS

This application is a continuation of U.S. patent application Ser. No. 12/272,411, filed Nov. 17, 2008, now U.S. Pat. No. 7,939,000, which is a continuation of U.S. patent application Ser. No. 10/873,085, filed Jun. 21, 2004, now U.S. Pat. No. 7,468,071, which is a continuation of U.S. patent application Ser. No. 10/000,583, filed Oct. 24, 2001, now U.S. Pat. No. 6,758,858, which is a division of U.S. patent application Ser. No. 08/833,797, filed Apr. 9, 1997, now U.S. Pat. No. 6,451,047, which is a continuation-in-part of two applications: 1) U.S. patent application Ser. No. 08/508,033, filed Jul. 27, 1995, now U.S. Pat. No. 5,749,880, which is a continuation-in-part of application U.S. patent application Ser. No. 08/401,871, filed Mar. 10, 1995, now U.S. Pat. No. 6,124,523; and 2) U.S. patent application Ser. No. 08/794,871, filed Feb. 5, 1997, now U.S. Pat. No. 6,039,755. This application expressly incorporates by reference the entirety of each of the above-mentioned applications as if fully set forth herein.

BACKGROUND OF THE INVENTION

The present invention relates generally to implantable intraluminal devices, particularly intraluminal stents. Because of the open lattice found in most intraluminal stents, a primary problem with these types of devices is occlusion of the vessel occurring after stent placement. Tissue ingrowth and neointimal hyperplasia significantly reduces the open diameter of the treated lumen over time, requiring additional therapies. The present invention incorporates the use of a biocompatible barrier material that prevents or delays the tissue ingrowth and neointimal hyperplasia, thus maintaining luminal patency for longer periods after initial treatment. The use of expanded polytetrafluoroethylene (ePTFE) as a bio-inert barrier material is well documented. In accordance with certain of its preferred embodiments, the present invention utilizes a radially expandable ePTFE material, such as that described in U.S. Pat. No. 6,039,755, to partially or fully embed the stent lattice, thereby providing a suitable barrier which improves stent patency.

The inventive intraluminal stent-graft device may be implanted either by percutaneous delivery using an appropriate delivery system, a cut-down procedure in which a surgical incision is made and the intraluminal device implanted through the surgical incision, or by laparoscopic or endoscopic or endoscopic delivery. More particularly the present invention relates to shape memory alloy and self-expanding endoluminal stents which are at least partially encapsulated in a substantially monolithic expanded polytetrafluoroethylene ("ePTFE") covering. In accordance with the present invention, an endoluminal stent, which has a reduced diametric dimension for endoluminal delivery and a larger in vivo final diametric diameter, is encapsulated in an ePTFE covering which circumferentially covers both the luminal and abluminal walls along at least a portion of the longitudinal extent of the endoluminal stent. The endoluminal stent is preferably fabricated from a shape memory alloy which exhibits either shape memory or pseudoelastic properties or from an elastic material having an inherent spring tension.

In a first embodiment of the invention, the endoluminal stent is encapsulated in the ePTFE covering in the stent's reduced diametric dimension and is balloon expanded in vivo to radially deform the ePTFE covering. The endoluminal stent may be either one which exhibits thermal strain recovery, pseudoelastic stress-strain behavior or elastic behavior at mammalian body temperature. While in its reduced diametric dimension the ePTFE encapsulating covering integrally constrains the endoluminal stent from exhibiting either thermal strain recovery, pseudoelastic stress-strain behavior or elastic behavior at mammalian body temperature. Radial deformation of the ePTFE covering releases constraining forces acting on the endoluminal stent by the undeformed ePTFE covering and permits the stent to radially expand.

In a second embodiment of the invention, an endoluminal stent fabricated of a shape memory alloy is encapsulated in its final diametric dimension and the encapsulated intraluminal stent-graft is manipulated into its reduced diametric dimension and radially expanded in vivo under the influence of a martensite to austenite transformation.

In a third embodiment of the present invention, a self-expanding intraluminal stent, fabricated of a material having an inherent spring tension, is encapsulated in its final diametric dimension and manipulated to a reduced diametric dimension and externally constrained for intraluminal delivery. Upon release of the external constraint in vivo the spring tension exerted by the self-expanding stent radially expands both the stent and the ePTFE encapsulating covering to a radially enlarged diameter.

In a fourth embodiment of the invention, the endoluminal stent is fabricated from a material having an inherent elastic spring tension and is encapsulated at a reduced dimension suitable for endoluminal delivery and balloon expanded in vivo to radially deform the ePTFE covering.

Shape memory alloys are a group of metallic materials that demonstrate the ability to return to a defined shape or size when subjected to certain thermal or stress conditions. Shape memory alloys are generally capable of being plastically deformed at a relatively low temperature and, upon exposure to a relatively higher temperature, return to the defined shape or size prior to the deformation. Shape memory alloys may be further defined as one that yields a thermoelastic martensite. A shape memory alloy which yields a thermoelastic martensite undergoes a martensitic transformation of a type that permits the alloy to be deformed by a twinning mechanism below the martensitic transformation temperature. The deformation is then reversed when the twinned structure reverts upon heating to the parent austenite phase. The austenite phase occurs when the material is at a low strain state and occurs at a given temperature. The martensite phase may be either temperature-induced martensite (TIM) or stress-induced martensite (SIM).

When a shape memory material is stressed at a temperature above the start of martensite formation, denoted $M_s$, where the austenitic state is initially stable, but below the maximum temperature at which martensite formation can occur, denoted $M_d$, the material first deforms elastically and when a critical stress is reached, it begins to transform by the formation of stress-induced martensite. Depending upon whether the temperature is above or below the start of austenite formation, denoted $A_s$, the behavior when the deforming stress is released differs. If the temperature is below $A_s$, the stress-induced martensite is stable; however, if the temperature is above $A_s$, the martensite is unstable and transforms back to austenite, with the sample returning to its original shape. U.S. Pat. Nos. 5,597,378, 5,067,957 and 4,665,906 disclose devices, including endoluminal stents, which are delivered in the stress-induced martensite phase of shape memory alloy and return to their pre-programmed shape by removal of the stress and transformation from stress-induced martensite to austenite.

Shape memory characteristics may be imparted to a shape memory alloy by heating the metal at a temperature above which the transformation from the martensite phase to the austenite phase is complete, i.e., a temperature above which the austenite phase is stable. The shape of the metal during this heat treatment is the shape "remembered." The heat treated metal is cooled to a temperature at which the martensite phase is stable, causing the austenite phase to transform to the martensite phase. The metal in the martensite phase is then plastically deformed, e.g., to facilitate its delivery into a patient's body. Subsequent heating of the deformed martensite phase to a temperature above the martensite to austenite transformation temperature, e.g., body temperature, causes the deformed martensite phase to transform to the austenite phase and during this phase transformation, the metal reverts back to its original shape.

The term "shape memory" is used in the art to describe the property of a material to recover a pre-programmed shape after deformation of a shape memory alloy in its martensitic phase and exposing the alloy to a temperature excursion through its austenite transformation temperature, at which temperature the alloy begins to revert to the austenite phase and recover its preprogrammed shape. The term "pseudoelasticity" is used to describe a property of shape memory alloys where the alloy is stressed at a temperature above the transformation temperature of the alloy and stress-induced martensite is formed above the normal martensite formation temperature. Because it has been formed above its normal temperature, stress-induced martensite reverts immediately to undeformed austenite as soon as the stress is removed, provided the temperature remains above the transformation temperature.

The martensitic transformation that occurs in the shape memory alloys yields a thermoelastic martensite and develops from a high-temperature austenite phase with long-range order. The martensite typically occurs as alternately sheared platelets, which are seen as a herringbone structure when viewed metallographically. The transformation, although a first-order phase change, does not occur at a single temperature but over a range of temperatures that varies with each alloy system. Most of the transformation occurs over a relatively narrow temperature range, although the beginning and end of the transformation during heating or cooling actually extends over a much larger temperature range. The transformation also exhibits hysteresis in that the transformations on heating and on cooling do not overlap. This transformation hysteresis varies with the alloy system.

A thermoelastic martensite phase is characterized by having a low energy state and glissile interfaces, which can be driven by small temperature or stress changes. As a consequence of this, and of the constraint due to the loss of symmetry during transformation, a thermoelastic martensite phase is crystallographically reversible. The herringbone structure of athermal martensite essentially consists of twin-related, self-accommodating variants. The shape change among the variants tends to cause them to eliminate each other. As a result, little macroscopic strain is generated. In the case of stress-induced martensite, or when stressing a self-accommodating structure, the variant that can transform and yield the greatest shape change in the direction of the applied stress is stabilized and becomes dominant in the configuration. This process creates a macroscopic strain, which is recoverable as the crystal structure reverts to austenite during reverse transformation.

The mechanical properties of shape memory alloys vary greatly over the transformation temperature range. Martensite phase alloys may be deformed to several percent strain at quite a low stress, whereas the austenite phase alloy has much higher yield and flow stresses. Upon heating after removing the stress, the martensite phase shape memory alloy will remember its unstrained shape and revert to its austenite phase.

Where a shape memory alloy is exposed to temperature above its transformation temperature, the martensite phase can be stress-induced. Once stress-induced martensite occurs, the alloy immediately strains and exhibits the increasing strain at constant stress behavior. Upon unloading of the strain however, the shape memory alloy reverts to austenite at a lower stress and shape recovery occurs, not upon the application of heat but upon a reduction of stress. This effect, which causes the material to be extremely elastic, is known as pseudoelasticity and the effect is nonlinear.

The present invention preferably utilizes an binary, equiatomic nickel-titanium alloy because of its biocompatibility and because such an alloy exhibits a transformation temperature within the range of physiologically-compatible temperatures. Nickel-titanium alloys exhibit moderate solubility for excess nickel or titanium, as well as most other metallic elements, and also exhibits a ductility comparable to most ordinary alloys. This solubility allows alloying with many of the elements to modify both the mechanical properties and the transformation properties of the system. Excess nickel, in amounts up to about 1%, is the most common alloying addition. Excess nickel strongly depresses the transformation temperature and increases the yield strength of the austenite. Other frequently used elements are iron and chromium (to lower the transformation temperature), and copper (to decrease the hysteresis and lower the deformation stress of the martensite). Because common contaminants such as oxygen and carbon can also shift the transformation temperature and degrade the mechanical properties, it is also desirable to minimize the amount of these elements.

As used in this application, the following terms have the following meanings:

$A_f$ Temperature: The temperature at which a shape memory alloy finishes transforming to Austenite upon heating.

$A_s$ Temperature: The temperature at which a shape memory alloy starts transforming to Austenite upon heating.

Austenite: The stronger, higher temperature phase present in NiTi.

Hysteresis: The temperature difference between a phase transformation upon heating and cooling. In NiTi alloys, it is generally measured as the difference between $A_p$ and $M_p$.

$M_f$ Temperature: The temperature at which a shape memory alloy finishes transforming to Martensite upon cooling.

$M_s$ Temperature: The temperature at which a shape memory alloy starts transforming to Martensite upon cooling.

Martensite: The more deformable, lower temperature phase present in NiTi.

Phase Transformation: The change from one alloy phase to another with a change in temperature, pressure, stress, chemistry, and/or time.

Shape Memory: The ability of certain alloys to return to a predetermined shape upon heating via a phase transformation.

Pseudoelasticity: The reversible non-linear elastic deformation obtained when austenitic shape memory alloys are strained at a temperature above $A_s$, but below $M_d$, the maximum temperature at which pseudoelasticity is obtained.

Thermoelastic Martensitic Transformation: A diffusionless, thermally reversible phase transformation characterized by a crystal lattice distortion.

BRIEF SUMMARY OF THE INVENTION

It is a principal objective of the present invention to encapsulate an intraluminal structural support with a substantially monolithic covering of ePTFE.

It is a further objective of the present invention to encapsulate a shape memory alloy intraluminal stent with a substantially monolithic covering of ePTFE.

It is another object of the present invention to provide a unique library of endoprostheses consisting generally of intraluminal structural supports made of shape memory alloys, which are at least partially encapsulated in a substantially monolithic expanded polytetrafluoroethylene covering, and which exhibit either thermal strain recovery, pseudoelastic stress-strain behavior or elastic behavior at mammalian body temperature.

It is a further objective of the present invention to encapsulate a shape memory alloy intraluminal stent at a reduced delivery diametric dimension and balloon expand the ePTFE encapsulated stent-graft to radially deform the ePTFE covering and release the radial constraint exerted by the ePTFE encapsulation on the shape memory stent thereby permitting the shape memory alloy stent to undergo transformation from its radially constrained dimension to an enlarged deployed dimension.

It is another objective of the present invention to encapsulate a shape memory alloy intraluminal stent at its enlarged diametric dimension, either with an at least partially unsintered tubular ePTFE extrudate having a diametric dimension comparable to the enlarged diametric dimension of the shape memory alloy intraluminal stent, or with a fully sintered ePTFE tubular member which has been radially expanded to a diametric dimension comparable to the enlarged diametric dimension of the shape memory alloy intraluminal stent, where the encapsulated intraluminal stent is then reduced in its diametric dimension for endoluminal delivery.

It is yet a further objective of the present invention to encapsulate a self-expanding intraluminal stent, such as a Gianturco stent or a pseudoelastic shape memory stent, at a reduced delivery diametric dimension and balloon expand the ePTFE encapsulated stent-graft to radially deform the ePTFE covering and release the radial constraint exerted by the ePTFE encapsulation on the self-expanding stent thereby permitting the self-expanding stent to elastically radially expand to its in vivo diameter.

It is another objective of the present invention to encapsulate a self-expanding intraluminal stent at its enlarged diametric dimension, either with an at least partially unsintered tubular ePTFE extrudate having a diametric dimension comparable to the enlarged diametric dimension of the shape memory alloy intraluminal stent, or with a fully sintered ePTFE tubular member which has been radially expanded to a diametric dimension comparable to the enlarged diametric dimension of the self-expanding intraluminal stent, and reducing the diametric dimension of the encapsulated stent for endoluminal delivery.

It is a still further objective of the present invention to encapsulate at a reduced delivery diametric dimension and balloon expand the ePTFE encapsulated stent-graft to radially deform the ePTFE covering and release the radial constraint exerted by the ePTFE encapsulation on the shape memory stent thereby permitting the stent to radially expand to a larger in vivo diametric dimension either by the shape memory property of the stent material or by elastic spring tension.

It is a further objective of the present invention to provide methods of encapsulating shape memory alloy intraluminal stents and self-expanding intraluminal stents, either at their reduced diametric dimension or at their in vivo diametric dimension.

It is another objective of the present invention to provide an ePTFE encapsulated intraluminal stent which is encapsulated between luminal and abluminal ePTFE tubular members, where the ePTFE tubular members may be applied to the intraluminal stent in their unsintered, partially sintered or fully sintered state.

It is a further objective of the present invention to employ an ePTFE interlayer positioned adjacent either the luminal or the abluminal surface of the intraluminal stent as a bonding adjuvant interlayer between the luminal and abluminal ePTFE tubular members.

BRIEF DESCRIPTION OF THE DRAWINGS

FIG. 1 is a perspective view of the ePTFE encapsulated intraluminal stent in accordance with the present invention.

FIG. 2A is a perspective view of an ePTFE encapsulated intraluminal stent encapsulated at its reduced diametric dimension for intraluminal delivery and balloon assisted expansion in vivo.

FIG. 2B is a perspective view of the ePTFE encapsulated intraluminal stent of FIG. 2A illustrating the ePTFE encapsulated intraluminal stent after balloon assisted expansion.

FIG. 3 is a side elevational, longitudinal cross-sectional view of the inventive ePTFE encapsulated intraluminal stent encapsulated at its nominal in vivo dimension.

FIG. 4 is a side elevational, longitudinal cross-sectional view of the inventive ePTFE encapsulated stent, illustrating the ePTFE encapsulated intraluminal stent partially at a reduced intraluminal delivery diameter deformed to a relatively reduced diameter suitable for intraluminal delivery, mounted on a delivery catheter having an axially moveable constraining sheath which constrains the ePTFE encapsulated self-expanding intraluminal stent in its relatively reduced diametric dimension.

DETAILED DESCRIPTION OF THE INVENTION

Figure 5:
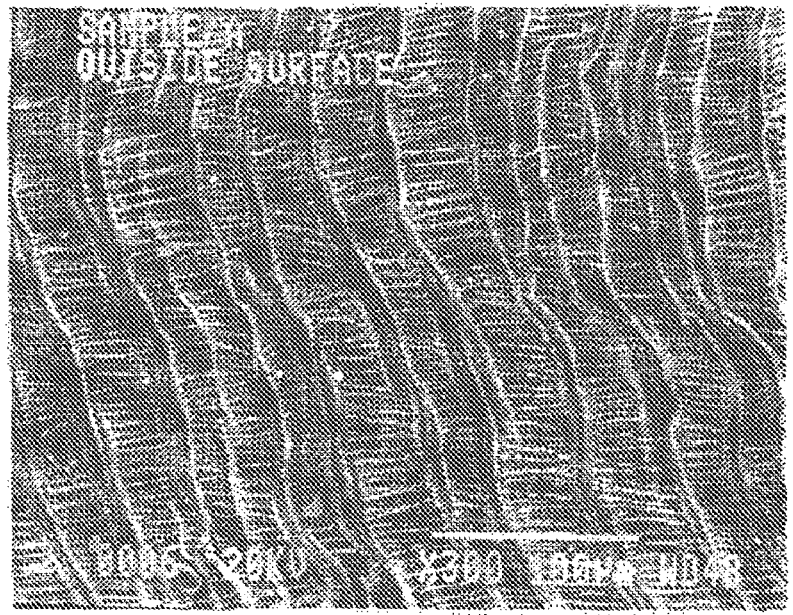
FIG. 5 is a scanning electron micrograph, taken at 300× magnification, of an outer surface of the radially expanded ePTFE material used to encapsulate the balloon assisted radially expandable encapsulated Nitinol stent of the present invention.

FIG. 1 illustrates the ePTFE encapsulated intraluminal stent 10 of the present invention in a radially enlarged diametric dimension. The inventive ePTFE encapsulated intraluminal stent 10 of the present invention is best illustrated with reference to several preferred embodiments thereof. The first preferred embodiment is depicted in FIGS. 2A-2B and consists generally of an intraluminal stent 12 made of a shape memory alloy which is at least partially encapsulated in a substantially monolithic ePTFE covering 14 while in a relatively smaller diametric dimension $D_1$ and is radially expandable in vivo under the influence of a radially outwardly directed force which radially deforms the ePTFE covering 14 and releases the stress exerted on the intraluminal stent 12 while at body temperature to permit the intraluminal stent to undergo deformation to a larger diametric dimension $D_2$.

FIGS. 3-4 generically depict the second, third and fourth preferred embodiments of the present invention an intraluminal stent 20 which is at least partially encapsulated within a substantially monolithic ePTFE covering 14 over at least an entire circumferential portion of the luminal and abluminal surfaces of the intraluminal stent 12. The second, third and fourth preferred embodiments differ from one another based upon the type of intraluminal stent 20 utilized and whether the encapsulated stent device is intended to radially expand in vivo under the influence of the shape memory behavior or elastic spring tension behavior of the intraluminal stent 20 or whether in vivo delivery will be balloon catheter assisted. Optionally, as discussed in the fifth preferred embodiment, an interlayer member made of at least partially unsintered ePTFE, such as ring-like member 23, may be interdisposed between an inner and outer ePTFE layer adjacent the intraluminal stent 20 to assist with the adhesion of the layers and/or to serve as a barrier between a radiopaque marker (not shown) and the intraluminal stent 20.

The second preferred embodiment of the present invention consists generally of an intraluminal stent 20 made of a shape memory alloy, which is at least partially encapsulated in a substantially monolithic ePTFE covering 14 while in a relatively larger diametric dimension $D_2$ and in the austenite phase. The at least partially encapsulated stent is then thermomechanically deformed at a temperature induced martensite phase to a smaller diametric dimension $D_1$ and is constrained by a constraining sheath 22 for endoluminal delivery. Once at the delivery site, the external constraint 22 is removed and the intraluminal stent 20 undergoes martensitic transformation to the austenite state and thermoelastically deforms 24 to its predetermined shape while unfolding or decompressing, without plastically deforming, the ePTFE covering 14, making contact with the luminal tissue (not shown).

The third preferred embodiment of the present invention consists generally of a self-expanding intraluminal stent 20 made from either an elastic spring material or of a pseudoelastic shape memory material, and is at least partially encapsulated in a substantially monolithic ePTFE covering 14 while in a relatively small diametric dimension $D_1$ such that the ePTFE encapsulating covering 14 acts to impart strain upon the intraluminal stent 20 and constrain the intraluminal stent from radial expansion to a relatively larger diametric dimension $D_2$ until intraluminally delivered, wherein the ePTFE covering 14 is radially deformed at body temperature, thereby releasing the strain exerted by the ePTFE covering 14 on the intraluminal stent 20, permitting the self-expanding intraluminal stent 20 to radially expand to a relatively larger diametric dimension $D_2$.

The fourth preferred embodiment of the present invention consists generally of a self-expanding intraluminal stent 20 made from either an elastic spring material or a pseudoelastic shape memory material, which is at least partially encapsulated in a substantially monolithic ePTFE covering 14 while in a relatively larger diametric dimension $D_2$ such that the ePTFE encapsulating covering 14 restrains the intraluminal stent from further self-expansion. The assembly is then worked, such as by crimping, calendering, folding, compressing or the like to reduce its diametric dimension to the reduced diametric dimension $D_1$, suitable for endoluminal delivery and constrained by an external constraining sheath 22. Once positioned at a desired intraluminal site, the constraining sheath 22 is removed to release the constraining force and the intraluminal stent is permitted to elastically expand as denoted by arrows 24, carrying the ePTFE covering 14 into contact with the intraluminal tissue (not shown).

Figure 9A:
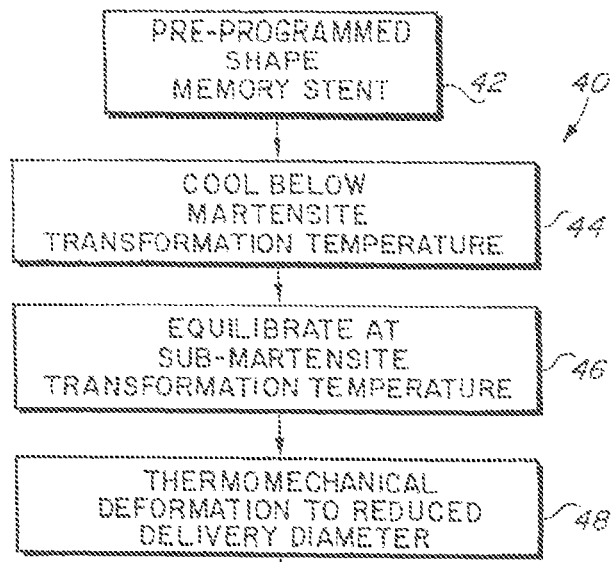
FIG. 9A is a flow diagram illustrating the inventive process steps to thermomechanically deform a pre-programmed shape memory stent to a reduced diametric dimension for encapsulation or endoluminal delivery.
Figure 9B:
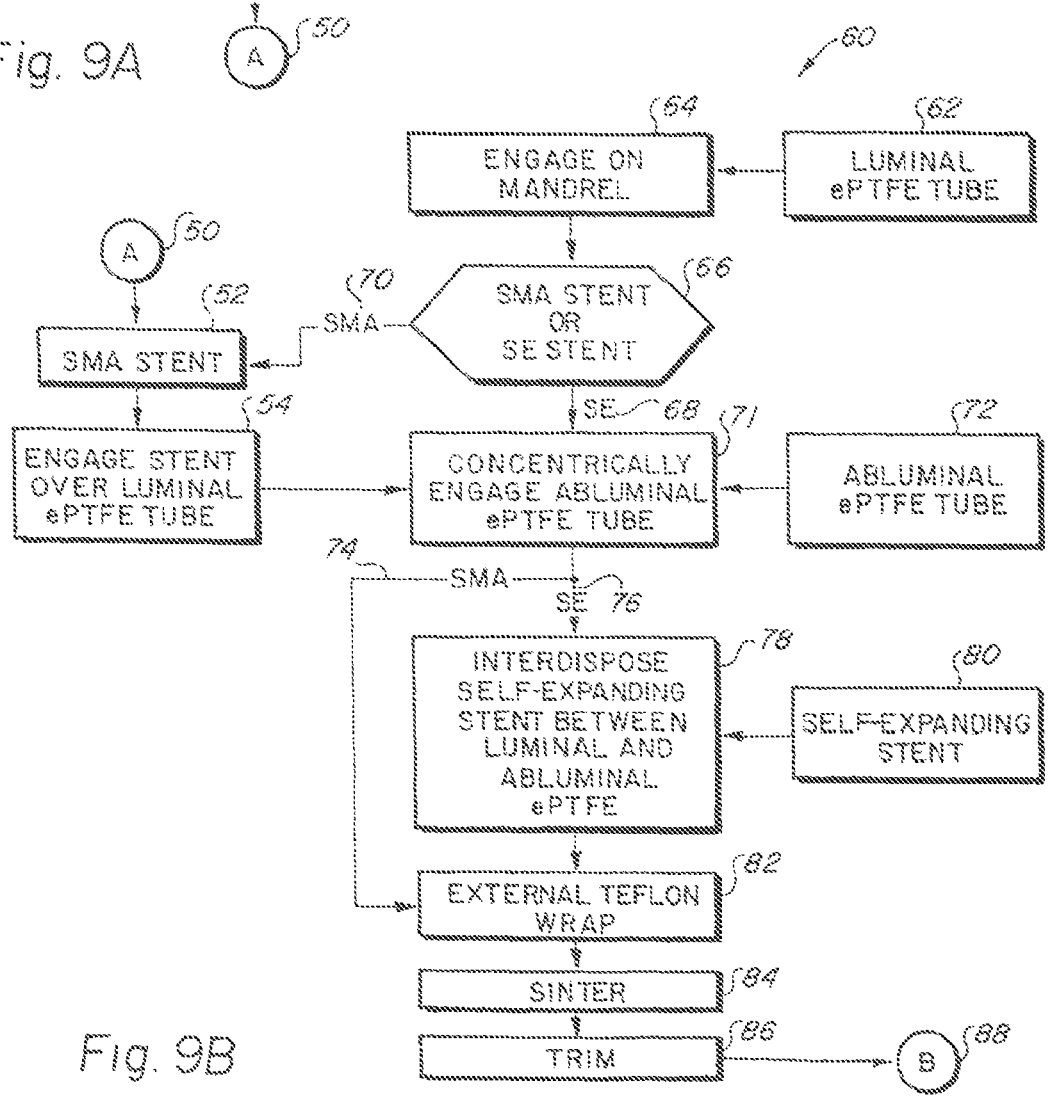
FIG. 9B is a flow diagram illustrating the inventive process steps to encapsulate a shape memory alloy stent and a self-expanding stent to make each preferred embodiment of the present invention.

As will be illustrated by the following examples and the accompanying process flow diagrams at FIGS. 9A and 9B, the methods for making each of the foregoing embodiments differ with each preferred embodiment. The difference in the methods is largely due to the selection of intraluminal stent type and whether the intraluminal encapsulated stent is intended for intraluminal delivery by balloon deformation of the ePTFE covering, whether delivery will occur due to the self-expanding property of the intraluminal encapsulated stent and non-deformation of the ePTFE covering or whether both delivery methods will be employed in succession.

First Embodiment

In accordance with a first preferred embodiment, illustrated in FIGS. 2A and 2B, there is provided a balloon expandable encapsulated shape memory alloy intraluminal stent 10. The balloon expandable encapsulated shape memory alloy intraluminal stent 10 consists generally of an endoluminal stent 12 fabricated of a shape memory alloy, preferably one having an $A_s$ value at a physiologically acceptable temperature compatible with tissue conservation, such as equiatomic nickel-titanium alloys known as Nitinol. The endoluminal stent 12 is at least partially encapsulated in a substantially monolithic ePTFE covering 14 while the endoluminal stent 12 is in a relatively smaller diametric dimension $D_1$. The substantially monolithic ePTFE covering 14 is a continuous integral tubular structure, is free of seams and covers at least part of both the luminal and abluminal surfaces about an entire circumferential section of the endoluminal stent 12 along at least a portion of the longitudinal axis of the intraluminal stent 12.

Figure 6:
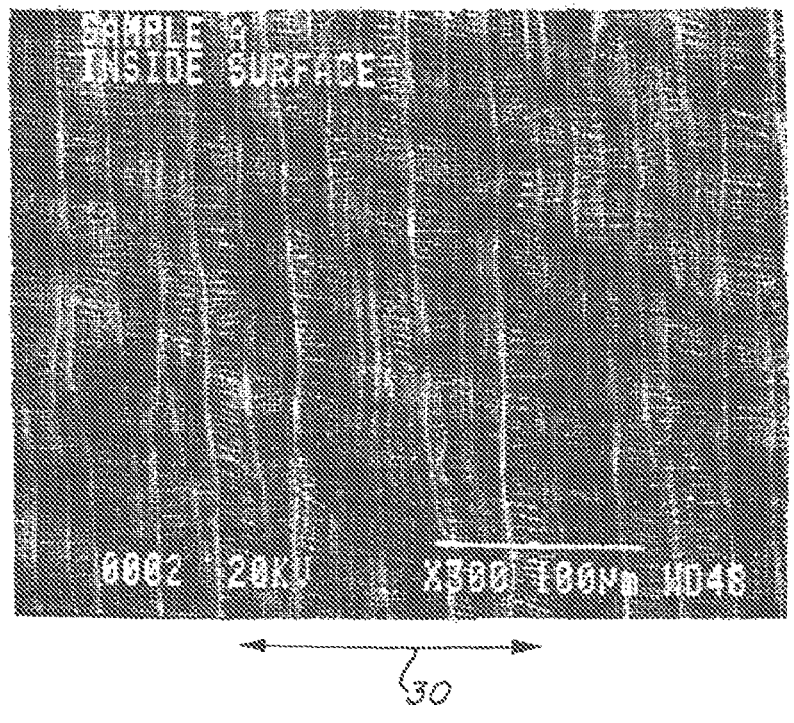
FIG. 6 is a scanning electron micrograph, taken at 300× magnification, of an inner surface of the ePTFE material used to encapsulate the balloon assisted radially expandable encapsulated Nitinol stent of the present invention.
Figure 7:
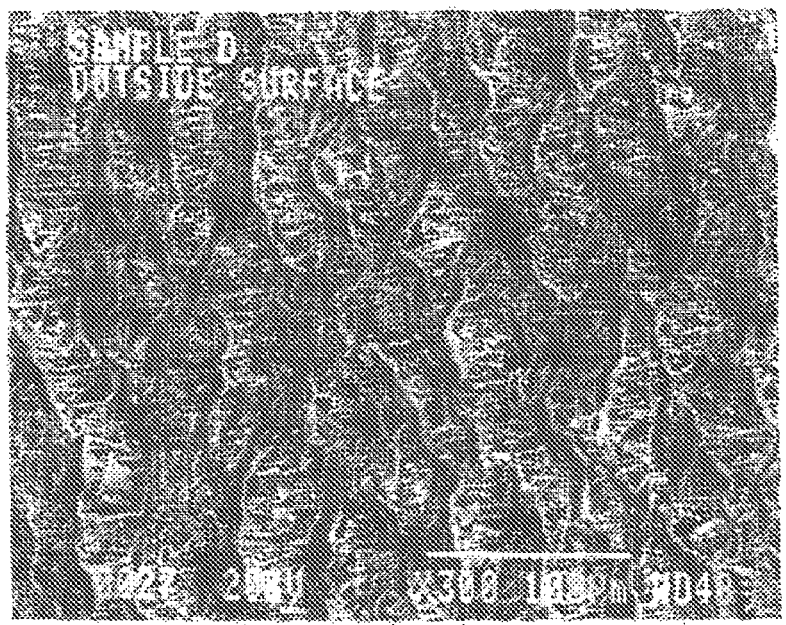
FIG. 7 is a scanning electron micrograph, taken at 300× magnification, of an outer surface of the ePTFE material used to encapsulate a self-expanding Nitinol or spring tension stent in accordance with the present invention.
Figure 8:
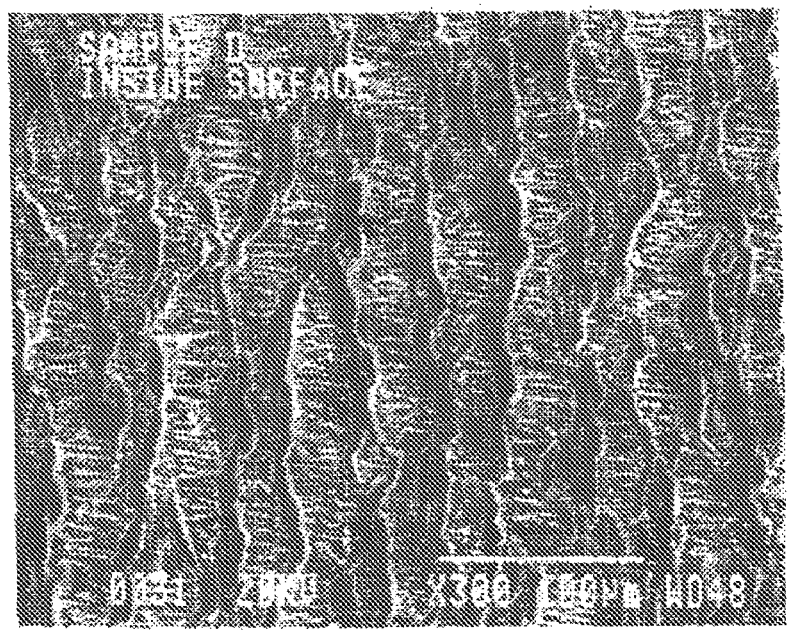
FIG. 8 is a scanning electron micrograph, taken at 300× magnification, of an inner surface of the ePTFE material used to encapsulate a self-expanding Nitinol or spring tension stent of the present invention.

As illustrated in FIGS. 5 and 6, the substantially monolithic ePTFE covering 14 is characterized by having a node and fibril microstructure where the nodes are oriented generally perpendicular to the longitudinal axis 30 of the stent 12 and the fibrils are oriented generally parallel to the longitudinal axis 30 of the stent 12, with the distance between adjacent nodes being termed the "internodal distance." As more fully described in U.S. Pat. Nos. 5,749,880 and 6,124,523, which are incorporated by reference, the substantially monolithic ePTFE covering 14 is preferably radially deformable at applied pressures less than about six atmospheres, most preferably less than about three atmospheres, due to the deformable nature of the nodes along their longitudinal axis, i.e., radial relative to the substantially monolithic ePTFE covering 14 and perpendicular to the longitudinal axis 30 of the intraluminal stent 12. The encapsulated intraluminal stent 10 is radially expandable in vivo under the influence of a radially outwardly directed force, such as from a balloon catheter, which radially deforms the ePTFE covering to a second relative large diametric dimension $D_2$, to release the constraining stress exerted on the intraluminal stent by the ePTFE covering while the encapsulated intraluminal stent 10 is at body temperature. The simultaneous release of the constraining force exerted by the ePTFE covering permits the intraluminal stent 12 to undergo thermomechanical deformation to a larger diametric dimension.

Example 1

Balloon Assisted Thermally Deployed Stent

A balloon assisted encapsulated shape memory alloy stent was constructed by longitudinally slitting about 5 cm of a 60 cm length of a first seamless unsintered expanded PTFE tube having an inner diameter of 3.0 mm. The slit ends were gripped into a fixture allowing the tube to hang vertically. At the opposite end of the tube, a length of wire was attached to assist in threading the tubing through the inner diameter of the stent. The thickness of the ePTFE layer was measured to be about 0.35 mm using a snap gauge. The ePTFE tube exhibited a node-fibril microstructure in which the fibrils were oriented parallel to the longitudinal axis of the tube throughout the wall thickness of the ePTFE tube.

A 10×40 mm shape memory endoluminal stent was placed in a cold, dry environment at approximately −40° C. and compressed about a mandrel having an outer diameter of 4.5 mm by mechanically deforming the stent to circumferentially conform to the outer diameter of the mandrel. The compressed stent was then removed from the cold, dry environment and concentrically passed over the outer diameter of the vertically hanging ePTFE tube, passing the wire through the stent lumen to assist in engaging the stent about the abluminal surface of the ePTFE tube without tearing or marring the ePTFE tube. A 3.3 mm diameter mandrel was then slid into the lumen of the ePTFE tube/stent assembly, and the tubing was secured to the mandrel using ½ inch strips of tetrafluoroethylene (TFE) tape. The assembly was then removed from the vertical hanging fixture.

A 60 cm length of a second seamless partially sintered ePTFE tube, having an inner diameter of 4.3 mm, slightly larger inner diameter than the outer diameter of the first ePTFE tube to provide an interference fit between the first and second ePTFE tubes, was slit longitudinally in the same manner as described above, and placed in the vertical hanging fixture. The mandrel bearing the first ePTFE tube and the shape memory stent was then passed into the lumen of the second tube, until the stent was approximately centered on the mandrel. The wall thickness of the second layer was measured as described above, and the thickness was found to be about 0.35 mm. Again, as with the first inner ePTFE layer, the fibrils were oriented parallel to the longitudinal axis of the tube. The ends of the second tube were also wrapped with strips of TFE tape to secure to the mandrel.

The assembly was then placed in a helical winding wrapping machine which tension wraps the assembly with a single overlapping layer of ½ inch TFE tape. The overlap of the winding was about 70%. The tension exerted by the TFE wrapping tape compressed the ePTFE/stent/ePTFE composite structure against the mandrel, thereby causing the layers of ePTFE to come into intimate contact through the interstices of the shape memory stent. The tension wrap was set to exert 1.7 psi pressure circumferentially around the ePTFE/stent/ePTFE and mandrel assembly.

The wrapped assembly was placed into a radiant heat furnace, which had been preheated to a 337° C. set point. The assembly remained in the furnace for about 7 minutes, and was removed. The heated assembly was allowed to cool for a period of time sufficient to permit manual handling of the assembly. After cooling, the TFE helical wrap was unwound from the sample and discarded. The ePTFE encapsulated stent assembly was then concentrically rotated about the axis of the mandrel to release any adhesion between the inner ePTFE layer and the mandrel. The ePTFE encapsulated stent assembly, still on the mandrel, was placed into a laser trimming fixture to trim excess ePTFE materials away from the proximal and distal ends. After trimming, the trimmed encapsulated stent was removed from the mandrel.

Five encapsulated stent samples were prepared in accordance with the foregoing description and were each placed on a 10 mm by 4 cm PTA balloon dilation catheter. The device was then placed into a temperature controlled water bath maintained at 37° C. The balloon was pressurized using a saline filled inflator, thereby expanding the encapsulated stent. Each encapsulated stent device was radially expanded under the influence of balloon deformation of the ePTFE encapsulating covering with full radial deformation to a 10 mm inner diameter occurring at inflation pressures between 2 and 4 atmospheres.

Example 2

Thin Wall Thermally Deployed Stent

The radially expanded encapsulated stents obtained from Example 1 were placed over a 10 mm diameter stainless steel mandrel, and spiral wrapped using ½ inch ePTFE tape as described above.

The wrapped assembly was placed again into a radiant heat furnace, which had been preheated to 337° C. set point. The assembly remained in the furnace for about 10 minutes and was removed. The heated assembly was allowed to cool for a period of time sufficient to permit manual handling of the assembly. After air cooling, the ends of the mandrel was engaged in two rings and the TFE helical wrap was unwound from the encapsulated stent samples and discarded. The encapsulated stents were concentrically rotated about the axis of the mandrel to release adhesion between the luminal ePTFE surface of the encapsulated stent and the mandrel.

The encapsulated stent was next cooled to about −20° C. in a cold dry environment and allowed to equilibrate for 30 minutes. The cooled encapsulated stent was then rolled between 2 plates to successively reduce the encapsulated stent inner diameter to about 3.5 mm, representing a reduction of about 40% from the radially expanded inner diameter of the encapsulated stent. The encapsulated stent at the reduced inner diameter of 3.5 mm was fully inserted into a constraining sheath having an inner diameter of approximately 3.7 mm.

The externally constrained encapsulated stent was then removed from the cold environment, and placed into a water bath maintained at a temperature of 37° C. A pusher rod was inserted into the constraining sheath and impinged upon one end of the constrained encapsulated stent. By passing the pusher rod through the constraining sheath, the encapsulated stent was ejected from the constraining sheath. As the stent was ejected, it radially dilated from its compressed state, and re-assumed the original fully expanded diametric dimension of about 10 mm inner diameter.

Second Embodiment

The second preferred embodiment of the present invention, depicted in FIGS. 3-4, consists generally of an intraluminal stent 20 made of a shape memory alloy which is at least partially encapsulated in a substantially monolithic ePTFE covering 14 while in a relatively larger diametric dimension $D_2$ and in the austenite phase, which is thermomechanically deformed to a temperature induced martensite phase and to a smaller diametric dimension $D_1$, and constrained by constraining sheath 22 for endoluminal delivery. Once at the delivery site, the constraint 22 is removed and the intraluminal stent 20 undergoes martensitic transformation to the austenite state and thermoelastically deforms 24 to its enlarged diametric dimension $D_2$ while unfolding the ePTFE covering 14 into contact with the luminal tissue (not shown).

Example 3

Thermally Self-Deploying Encapsulated Stent

A thermally deployed encapsulated shape memory alloy stent was constructed by placing a 40 cm length of a first seamless expanded PTFE tube over a 10 mm cylindrical stainless steel mandrel. The inner diameter of the ePTFE tube was of a sufficient size to permit an interference fit with the mandrel. The thickness of the ePTFE layer was measured to be about 0.20 mm by taking a radial slice of the seamless tube, and evaluated by light microscopy incorporating a calibrated reticle. The ePTFE tube has a node-fibril microstructure in which the fibrils are oriented perpendicular to the longitudinal axis of the mandrel throughout the wall thickness of the ePTFE tube. The ends of the ePTFE tube were wrapped with TFE tape to keep the tube from sliding along the mandrel for the next assembly step. A shape memory alloy stent having a nominal inner diameter of about 10 mm and being about 100 mm in length in its enlarged diametric configuration was concentrically placed over the ePTFE covered mandrel at about 22° C. and positionally centrally along the longitudinal length of the ePTFE tube. The inner diameter of the shape memory stent was toleranced to the outer diameter of the ePTFE tube on the mandrel and engaged about the ePTFE tube without tearing or disturbing the surface of the ePTFE tube. A second seamless ePTFE tube having a wall thickness of 0.20 mm, measured as described above, was concentrically engaged over the stent and the first ePTFE tube by first making diametrically opposed longitudinal slits in one end of the second ePTFE tube and concentrically inserting the mandrel/first ePTFE tube/stent assembly into the lumen of the second tube. Again, as with the first ePTFE tube, the second ePTFE tube exhibited a node-fibril microstructure in which the fibrils were oriented parallel to the longitudinal axis of the second ePTFE tube throughout the wall thickness of the second ePTFE tube. The opposing ends of the second ePTFE tube were secured about the first ePTFE tube and the mandrel by tension wrapping with strips of TFE tape.

The entire assembly was then placed in a helical winding tension wrapping machine, which tension wrapped the assembly with a single overlapping layer of ½ inch TFE tape in the same manner as in Example 1 to compress the ePTFE material from the first and second ePTFE tubes into intimate contact with one another through the wall openings of the stent. The wrapped assembly was placed into a radiant heat furnace, which had been preheated to about a 337° C. set point. The assembly remained in the furnace for about 10 minutes, and was removed. The heated assembly was allowed to cool for a period of time sufficient to permit manual handling of the assembly. After cooling, the ends of the mandrel were engaged in two rings and the TFE helical wrap was unwound from the encapsulated stent assembly and discarded. The encapsulated stent assembly was then circumferentially rotated about the axis of the mandrel to break any adhesion "occurring between the luminal ePTFE material and the mandrel. Excess ePTFE material from the proximal and distal ends of the encapsulated stent assembly was then laser trimmed in the manner described in Example 1 and the encapsulated stent assembly was removed from the mandrel.

The encapsulated stent was then cooled to about −20° C. in a cold dry environment and allowed to equilibrate for 30 minutes. The encapsulated stent was then flattened between 2 plates to bring diametrically opposed luminal wall surfaces of the encapsulated stent into contact with one another, thereby creating a flat structure without an inner lumen. The encapsulated stent was then folded over itself along its longitudinal axis once, and then again for a total of one flattening operation and two folding operations. Thus, the diameter of the embedded stent was reduced about 60% from its original post-encapsulated diameter. While still in the cold, dry environment, the device was fully inserted into a constraining sheath with an internal diameter of approximately 4.7 mm.

The folded and sheathed stent was then removed from the cold environment and placed into a water bath maintained at a temperature of 37° C. A pusher was inserted into the lumen of the constraining sheath and the encapsulated stent was ejected from the constraining sheath as described above in Example 2. As the stent was ejected, it unfolded from its flattened and folded state, and re-assumed the original tubular diametric configuration having a nominal inner diameter of 10 mm.

Third Embodiment

The third preferred embodiment of the present invention, depicted in FIGS. 2A-2B, consists generally of self-expanding intraluminal stent 12 made from either an elastic spring material or of a pseudoelastic shape memory material, and is at least partially encapsulated in a substantially monolithic ePTFE covering 14 while in a relatively small diametric dimension $D_1$, such that the ePTFE encapsulating covering 14 acts to impart strain upon the intraluminal stent 12 and constrain the intraluminal stent 12 from radial expansion to a relatively larger diametric dimension $D_2$. Until it is intraluminally delivered and the ePTFE encapsulation 14 radially deformed at body temperature to release the strain exerted by the ePTFE covering 14, the self-expanding intraluminal stent 12 cannot radially deform to a relatively larger diametric dimension $D_2$.

Example 4

Elastic Spring Balloon Deployed Encapsulated Stent

An encapsulated elastically self-expanding stainless steel stent was constructed by placing a 30 cm length of seamless unsintered ePTFE tube over a 3.3 mm cylindrical stainless steel mandrel. The inner diameter of the ePTFE tube was toleranced to provide a slight interference fit to the mandrel. The thickness of the ePTFE layer was measured to be about 0.35 mm by direct measurement of seamless tube wall using a snap gauge. The ePTFE tube exhibited a node-fibril microstructure in which the fibrils were oriented parallel to the longitudinal axis ePTFE tube throughout the wall thickness of the ePTFE tube. The ends of the ePTFE tube were wrapped with strips of TFE tape to retain the position of the ePTFE tube on the mandrel for the next assembly step. A second seamless sintered ePTFE tube was concentrically engaged over the first ePTFE tube by first longitudinally slitting opposing ends of the ends of the second tube, then inserting the mandrel and first ePTFE tube into the lumen of the second ePTFE tube. One end of the second ePTFE tube was wrapped with strips of ½ inch TFE tape to secure it to the first ePTFE tube and the mandrel. The wall thickness of the second ePTFE tube was measured as described above, and the thickness was found to be about 0.35 mm. As with the first ePTFE tube, the second ePTFE tube exhibited a node-fibril microstructure in which the fibrils were oriented parallel to the longitudinal axis of the ePTFE tube.

An elastic spring stainless steel stent having a nominal inner diameter of about 15 mm and a length of about 24 mm in its enlarged diametric configuration was inserted into a constraining sheath to reduce the inner diameter to about 4.0 mm. A small length of the stent is left exposed from one end of the constraining sheath. The constraining sheath containing the radially constrained stent was inserted over the mandrel and forced between the first and second ePTFE tubes such that it was positioned intermediate to the first and second ePTFE tubes. The exposed end of the stent was then frictionally engaged through the second ePTFE tube wall and the constraining sheath was retracted, leaving the stent positioned between the first and second ePTFE tubes. The unsecured end of the second ePTFE tube was then secured to the first ePTFE tube and the mandrel with strips of ½ inch TFE tape.

The assembly was then placed in a helical winding machine to tension wrap a single overlapping layer of ½ inch TFE tape, and sintered in a radiant heat furnace, cooled, the TFE tape unwrapped and the excess ePTFE laser trimmed as described in Example 1 above. The resulting encapsulated stent was placed over the balloon on a 12 mm by 4 cm PTA balloon dilation catheter. The device was then placed into a temperature controlled water bath maintained at 45° C. The balloon was pressurized using a saline filled inflator which radially deformed the ePTFE encapsulation and permitted radial expansion of the elastically self-expanding stent. The encapsulated stent fully radially expanded to a 12 mm inner diameter at an applied pressure of 2.5 atmospheres.

Fourth Embodiment

The fourth preferred embodiment of the present invention, also representatively depicted in FIGS. 3-4, consists generally of a self-expanding intraluminal stent 20 made from either an elastic spring material or a pseudoelastic shape memory material, which is at least partially encapsulated in a substantially monolithic ePTFE covering 14 while in a relatively larger diametric $D_2$ dimension, such that the ePTFE encapsulating covering 14 acts as to restrain the intraluminal stent 20 from further self-expansion. The encapsulated assembly is then worked, such as by crimping, calendering, folding, or the like, to its reduced diametric dimension $D_1$, to achieve a profile suitable for endoluminal delivery, and the assembly is then constrained by an external constraining sheath 22. Once positioned at a desired intraluminal site, the constraining sheath 22 is removed to release the constraining force and the intraluminal stent 20 is permitted to elastically expand 24, carrying the ePTFE covering 14 into contact with the intraluminal tissue (not shown).

Example 5

Stress-Induced Martensite Self-Deploying Encapsulated Stent

A self deploying encapsulated shape memory alloy stent is constructed by placing a 40 cm length of seamless expanded PTFE tube over a 10 mm cylindrical stainless steel mandrel. The inner diameter of the ePTFE tube is closely toleranced to provide a slight interference fit to the mandrel. The thickness of the ePTFE layer is measured to be about 0.20 mm by taking a radial slice of the seamless tube, and evaluated by light microscopy incorporating a calibrated reticle. The tubing is constructed such that the fibrils are oriented perpendicular to the longitudinal axis of the mandrel. The ends of the seamless tube are wrapped with strips of TFE tape to keep the tube from sliding along the mandrel for the next assembly step. A shape memory alloy stent about 10 mm inner diameter by 100 mm in length in its enlarged diametric configuration is placed over the ePTFE covered mandrel at about 22° C. and centered over the ePTFE layer. The inner diameter of the shape memory stent is closely toleranced to the outer diameter of the ePTFE covered mandrel. A second tube of seamless expanded PTFE is placed over the stent by slitting the ends of the second tube, and inserting the mandrel, ePTFE tube, and stent assembly into the second tube. The wall thickness of the second layer is measured as described above, and the thickness is found to be about 0.20 mm. Again, as with the first inner ePTFE layer, the fibrils are oriented perpendicular to the longitudinal axis of the mandrel. The ends of the second tube are also wrapped with strips of TFE tape.

The assembly is then placed in a helical winding machine, which wraps the assembly with a single overlapping layer of ½ inch TFE tape. The overlap of the winding was about 70%. The wrapping material compresses the ePTFE/stent/ePTFE composite structure against the mandrel, causing the layers of ePTFE to come into intimate contact through the interstices of the shape memory stent.

The wrapped assembly is placed into a radiant heat furnace, which is preheated to a 337° C. set point. The assembly remains in the furnace for about 10 minutes, and is removed. The heated assembly is allowed to cool for a period of time sufficient to permit manual handling of the assembly. After cooling, the ends of the mandrel are engaged in two rings, allowing the TFE helical wrap to be unwound from the sample and discarded. The ePTFE/stent assembly is then rotated about the axis of the mandrel to break the grip of the inner ePTFE layer to the mandrel. The stent sample, while still on the mandrel, is placed into a fixture to allow for laser trimming of the ePTFE materials away from the embedded stent. Trimming operation is performed on both ends of the device. After trimming, the embedded and trimming stent was removed from the mandrel.

The encapsulated stent was then rolled between 2 plates, reducing the diameter of the stent to about 3.5 mm. Thus, the diameter of the embedded stent was reduced about 40% from its original post encapsulation diameter. While in the compressed state, the device was fully inserted into a constraining sheath with an internal bore of approximately 3.7 mm. The constrained stent was then placed into a water bath maintained at a temperature of 37° C. A pusher was inserted into the bore of the sheath, and the stent was ejected from the constraining sheath. As the stent was ejected, it unfurled from its flattened and folded state, and re-assumed the original post-encapsulation tubular diametric configuration.

Fifth Embodiment

In accordance with a fifth preferred embodiment of the inventive encapsulated stent, an at least partially unsintered tubular interlayer is interdisposed between the inner and outer ePTFE layers and adjacent the intraluminal stent along at least a longitudinal extent thereof. The interlayer member may consist of a single tubular member which extends along at least a portion of the longitudinal axis of the intraluminal stent. Alternatively, the interlayer member may consist of a plurality of ring-like members positioned along the longitudinal axis of the intraluminal stent and in spaced-apart relationship from one and other. The interlayer member may be preferably employed either: i) where at least one of the inner and outer ePTFE tubular members of the inventive encapsulated intraluminal stent is fully sintered to assist in formation of a monolithic joining of the inner and outer ePTFE tubular members, and/or 2) to serve as a barrier between a radiopaque marker and the intraluminal stent to insulate against galvanic corrosion resulting from contact of metal atoms in a radiopaque marker and metal in an intraluminal stent. The interlayer member may be employed with any type of intraluminal stent, i.e., a shape memory alloy which behaves in either a thermoelastic or pseudoelastic manner, a self-expanding stent in which radial expansion is a spring tension mediated event, or a balloon expandable stent.

Example 6

Thermally Self-Deploying Encapsulated Stent

A thermally deployed encapsulated shape memory alloy stent was constructed by placing a 40 cm length of a first sintered seamless expanded PTFE tube over a 10 mm cylindrical stainless steel mandrel. The inner diameter of the ePTFE tube was of a sufficient size to permit an interference fit with the mandrel. The thickness of the ePTFE layer was measured to be about 0.20 mm by taking a radial slice of the seamless tube, and evaluated by light microscopy incorporating a calibrated reticle. The ePTFE tube exhibited a node-fibril microstructure in which the fibrils were oriented parallel to the longitudinal axis of the mandrel throughout the wall thickness of the ePTFE tube. The ends of the ePTFE tube were wrapped with TFE tape to keep the tube from sliding along the mandrel for the next assembly step. A shape memory alloy stent having a nominal inner diameter of about 10 mm and being about 100 mm in length in its enlarged diametric configuration was concentrically placed over the ePTFE covered mandrel at about 22° C. and positionally centrally along the longitudinal length of the ePTFE tube. The inner diameter of the shape memory stent was toleranced to the outer diameter of the ePTFE tube on the mandrel and engaged about the ePTFE tube without tearing or disturbing the surface of the ePTFE tube. A pair of unsintered ePTFE rings, prepared by wrapping unsintered ePTFE films (sheets) concentrically about each of the opposing ends of the shape memory alloy stent and the first sintered ePTFE tube, were wrapped such that the node and fibril microstructure of the unsintered ePTFE rings had a fibril orientation perpendicular to the fibril orientation of the first ePTFE tube and the longitudinal axis of the stent.

A second sintered seamless ePTFE tube, having a wall thickness of 0.20 mm, measured as described above, was concentrically engaged over the entire length of the stent, the pair of unsintered ePTFE rings and the first ePTFE tube by first making diametrically opposed longitudinal slits in one end of the second ePTFE tube and concentrically inserting the mandrel/first ePTFE tube/stent assembly into the lumen of the second tube. Again, as with the first ePTFE tube, the second ePTFE tube exhibited a node-fibril microstructure in which the fibrils were oriented parallel to the longitudinal axis of the second ePTFE tube throughout the wall thickness of the second ePTFE tube. The opposing ends of the second ePTFE tube were secured about the first ePTFE tube and the mandrel by tension wrapping with strips of TFE tape.

The entire assembly was then placed in a helical winding tension wrapping machine which tension wrapped the assembly with a single overlapping layer of ½ inch TFE tape in the same manner as in Example 1 to compress the ePTFE material from the first and second ePTFE tubes into intimate contact with one another through the wall openings of the stent.

The wrapped assembly was placed into a radiant heat furnace, which had been preheated to about a 337° C. set point. The assembly remained in the furnace for about 10 minutes and was removed. The heated assembly was allowed to cool for a period of time sufficient to permit manual handling of the assembly. After cooling, the ends of the mandrel were engaged in two rings and the TFE helical wrap was unwound from the encapsulated stent assembly and discarded. The encapsulated stent assembly was then circumferentially rotated about the axis of the mandrel to break any adhesion occurring between the luminal ePTFE material and the mandrel. Excess ePTFE material from the proximal and distal ends of the encapsulated stent assembly was then laser trimmed in the manner described in Example 1 and the encapsulated stent assembly was removed from the mandrel.

The encapsulated stent was then cooled to about −20° C. in a cold dry environment and allowed to equilibrate for 30 minutes. The encapsulated stent was then flattened between 2 plates to bring diametrically opposed luminal wall surfaces of the encapsulated stent into contact with one another, thereby creating a flat structure without an inner lumen. The encapsulated stent was then folded over itself along its longitudinal axis once, and then again for a total of one flattening operation and two folding operations. Thus, the diameter of the embedded stent was reduced about 60% from it original post encapsulated diameter. While still in the cold, dry environment, the device was fully inserted into a constraining sheath with an internal diameter of approximately 4.7 mm.

The folded and sheathed stent was then removed from the cold environment, and placed into a water bath maintained at a temperature of 37° C. A pusher was inserted into the lumen of the constraining sheath and the encapsulated stent was ejected from the constraining sheath as described above in Example 2. As the stent was ejected, it unfolded from its flattened and folded state, and re-assumed the original tubular diametric configuration having a nominal inner diameter of 10 mm.

While the interlayer member employed in the foregoing Example 6 were rings produced from wrapping sheets of unsintered ePTFE material, it will also be appreciated that tubular or ring-like unsintered ePTFE members may be employed. Where the interlayer member is a tubular or ring-like unsintered ePTFE member, the interlayer member will preferably have a node and fibril microstructure in which the fibril orientation of the interlayer member is parallel to the longitudinal axis of the interlayer member and parallel with the fibril orientation of the inner and outer ePTFE tubular members which the interlayer member is interdisposed between. This co-parallel arrangement of the fibril orientations of the interlayer member and the inner and outer ePTFE tubular members permits the resulting encapsulated stent device to be further radially expanded by balloon expansion in order to further model the in vivo profile to the receiving anatomical structure at radial expansion pressures comparable to that of the balloon assisted encapsulated stent embodiments described above.

Where a thermoelastic transformation of a shape memory intraluminal stent is desired, care must be taken to: 1) avoid imparting a secondary shape memory to the shape memory alloy during sintering of the ePTFE encapsulating covering, 2) avoid inducing stress-induced martensite formation during thermomechanical forming for either encapsulation or mounting onto a delivery catheter, and 3) avoid inducing non-recoverable strains by exceeding the strain limit of the shape memory alloy material used. Where the elastic behavior of a stent made of either a pseudoelastic shape memory alloy or a spring tension material, care must be taken to avoid plastically deforming the stent which would deleteriously effect the elastic deformation property of the intraluminal stent during intraluminal delivery. Finally, where the pseudoelastic behavior of an intraluminal stent made of a shape memory material is to be utilized in the encapsulated intraluminal stent, care must be taken to maintain the temperature of the shape memory alloy above $A_f$, but below $M_d$ during either the process of encapsulating the stent at a reduced diameter, and before sintering, for balloon expansion in vivo or during deformation of the encapsulated stent to a reduced delivery diameter for loading onto a delivery catheter. In this manner, the stress-induced martensite phase will be induced in the shape memory alloy during deformation of the stent to a diametric dimension suitable for endoluminal delivery and maintained so that when the encapsulated stent, in the stress-induced martensite state, is delivered and either the ePTFE constraint or the constraining sheath is relieved, the strain is released and the stent, in the stress-induced martensite phase, is permitted to transform to austenite and the stent to elastically deform to its pre-programmed diametric dimension.

The methods described in the foregoing Examples are summarized in FIGS. 9A-9B, which are process flow diagrams setting forth the fundamental method steps of the methods to make each of the above-described preferred embodiments. Where a shape memory intraluminal stent is to be encapsulated in an ePTFE covering and thermoelastic transformation of the shape memory stent is desired, either in a balloon assisted expandable encapsulated stent embodiment or in a self-expanding encapsulated stent embodiment, the thermoelastic deformation of the shape memory stent from its enlarged diametric dimension $D_2$, to its reduced diametric dimension $D_1$, may be accomplished in accordance with the method 40 set forth in FIG. 9A. Thermoelastic deformation method 40 entails first providing an shape memory alloy intraluminal stent having a predetermined shape memory configuration 42. The intraluminal stent is then exposed to a temperature below the martensite transformation temperature $M_s$ of the shape memory alloy 44 and allowed to equilibrate at the sub-martensite transformation temperature $M_s$ 46. While still below the $M_s$ temperature, the stent is mechanically deformed 48 to reduce its diameter from the enlarged diametric dimension $D_2$ to a reduced diametric dimension $D_1$ suitable for endoluminal delivery. The stent at its reduced diametric dimension 50 is now at a dimensional state suitable for encapsulation at its reduced diametric dimension $D_1$.

The encapsulation method 60 is more fully set forth in FIG. 9B, and is applicable for either a shape memory alloy intraluminal stent which is to be encapsulated either at its reduced diametric dimension $D_1$, or at its enlarged diametric dimension $D_2$, as well as for a self-expanding stent which radially expands due to inherent spring tension in the stent. A luminal ePTFE tube 62 is concentrically engaged upon a mandrel 64 and secured to the mandrel. Either a shape memory stent 52 or a self-expanding stent 80 is selected at step 66. If a shape memory stent is selected 70, the shape memory stent 52 is engaged over the luminal ePTFE tube at step 54 while maintaining the stent at a temperature below $A_s$ to prevent the stent. from radially expanding. If a self-expanding stent 80 is selected 68, an abluminal ePTFE tube is concentrically engaged over the luminal ePTFE tube and the self-expanding stent 80 interdisposed between the luminal and abluminal ePTFE tubes and secured there between 78. Where a shape memory alloy intraluminal stent is employed 74, the abluminal ePTFE tube is concentrically engaged over the stent. Once the stent is positioned intermediate between the luminal and abluminal ePTFE tubes, the entire assembly is then wrapped with TFE tape 82 to exert a circumferential pressure about the entire circumference of both the luminal and abluminal ePTFE tubes and the stent, causing the ePTFE tubes to be motivated into intimate contact with one and other through the interstices of the stent. The entire wrapped assembly is then sintered 84 and excess ePTFE overlaying ends of the stent may be trimmed 86.

Once trimmed, the encapsulated stent is then prepared for mounting onto a delivery catheter 88, either by mounting the encapsulated stent in its reduced diametric dimension $D_1$ onto a balloon catheter for balloon-assisted delivery, or by thermomechanical deformation from the enlarged diametric dimension $D_2$ to the reduced diametric dimension $D_1$, following the method steps of thermomechanical deformation 40 or formation of stress-induced martensite for pseudoelastic recovery by crimping, folding or otherwise reducing the encapsulated stent to its reduced diametric dimension $D_1$, mounting onto a delivery catheter and applying an external constraining sheath concentrically over the encapsulated stent.

Those skilled in the art will understand and appreciate that while the present invention has been described with reference to its preferred embodiments and the examples contained herein, certain variations in material composition, shape memory alloy constitution, stent and ePTFE dimensional size and configuration, temperatures, times and other operational and environmental conditions may be made without departing from the scope of the present invention which is limited only by the claims appended hereto. For example, one skilled in the art will understand and appreciate from the foregoing that the methods for making each of the foregoing embodiments differs with each preferred embodiment. These differences in the methods are largely due to the selection of intraluminal stent type and whether the intraluminal encapsulated stent is intended for initial intraluminal delivery by balloon expansion or whether initial delivery will occur due to the self-expanding property of the intraluminal encapsulated stent.

The invention claimed is:

1. A method for making an encapsulated stent, comprising:
   providing a first seamless unsintered ePTFE tube;
   providing a second seamless sintered ePTFE tube;
   positioning a self-expanding stent between the first and second ePTFE tubes to form an assembly;
   disposing an ePTFE interlayer member between the first and second ePTFE tubes; and
   joining the first ePTFE tube to the second ePTFE tube through openings in a wall of the stent by applying first pressure, and then heat, to the assembly.

2. The method according to claim 1, wherein the disposing step includes positioning the ePTFE interlayer member adjacent an abluminal surface of the stent.

3. The method according to claim 1, wherein the disposing step includes positioning the ePTFE interlayer member adjacent a luminal surface of the stent.

4. The method according to claim 1, wherein the ePTFE interlayer member comprises a plurality of ring-shaped members, the disposing step including positioning the ring-shaped members along a longitudinal axis of the stent in spaced relation from one another.

5. The method according to claim 1, further comprising the step of inserting a radiopaque marker between the first and second ePTFE tubes, the disposing step including positioning the ePTFE interlayer member between the radiopaque marker and the stent.

6. The method according to claim 1, wherein the interlayer member comprises an unsintered film, the step of disposing comprising wrapping the film about an end of the stent.

7. The method according to claim 1, wherein the interlayer member comprises a tubular unsintered member, the step of disposing comprising positioning the member in coaxial relation with an end of the stent.

8. The method according to claim 7, wherein the tubular unsintered member has a node-fibril microstructure including fibrils having a generally uniaxial orientation, the step of disposing comprising orienting the fibrils parallel to a longitudinal axis of the assembly.

9. The method according to claim 8, wherein the first and second ePTFE tubes, characterized by a node-fibril microstructure, contain fibrils having a parallel orientation with respect to the longitudinal axis.

10. The method according to claim 1, further comprising:
placing the first seamless unsintered ePTFE tube over a mandrel; and
concentrically engaging the second seamless sintered ePTFE tube over the first ePTFE tube after placing the first ePTFE tube over the mandrel, the positioning step including manipulating the stent from a first diameter to a second diameter smaller than the first diameter and inserting the stent between the first ePTFE tube and second ePTFE tube to form the assembly, the joined first ePTFE tube and second ePTFE tube applying a constraining force on the stent, following the joining step, to prevent expansion of the stent from the second diameter to the first diameter.

11. The method according to claim 10, wherein the placing step further comprises wrapping the ends of the ePTFE tube with strips of tape to retain the position of the ePTFE tube on the mandrel.

12. The method according to claim 10, wherein the stent comprises a shape memory material, the positioning step including cooling the stent to a temperature below its martensitic transformation temperature prior to manipulating to the second diameter.

13. The method according to claim 10, wherein the stent comprises a shape memory material, the positioning step including maintaining the temperature of the stent above its martensitic transformation temperature during the manipulating to the second diameter.

14. The method according to claim 1, the stent having a first diameter and a second diameter smaller than the first diameter, the positioning step performed at the stent first diameter, further comprising the step of manipulating the assembly to the stent second diameter, following the joining step, and inserting the assembly into a delivery sheath that applies a constraining force on the assembly to prevent expansion thereof.

15. The method according to claim 14, wherein the stent comprises a shape memory material, the manipulating step including cooling the stent to a temperature below its martensitic transformation temperature.

16. The method according to claim 14, wherein the stent comprises a shape memory material, the manipulating step including maintaining the temperature of the stent above its martensitic transformation temperature.

* * * * *